(12) United States Patent
Baust et al.

(10) Patent No.: US 9,408,654 B2
(45) Date of Patent: Aug. 9, 2016

(54) MODULAR PULSED PRESSURE DEVICE FOR THE TRANSPORT OF LIQUID CRYOGEN TO A CRYOPROBE

(75) Inventors: John M. Baust, Owego, NY (US); John G. Baust, Owego, NY (US); Roy Cheeks, Harper's Ferry, WV (US); Anthony Robilotto, Binghamton, NY (US); Kristi Snyder, Candor, NY (US)

(73) Assignee: Endocare, Inc., Austin, TX (US)

( * ) Notice: Subject to any disclaimer, the term of this patent is extended or adjusted under 35 U.S.C. 154(b) by 939 days.

(21) Appl. No.: 12/553,005

(22) Filed: Sep. 2, 2009

(65) Prior Publication Data

US 2010/0057067 A1 Mar. 4, 2010

Related U.S. Application Data (60) Provisional application No. 61/093,916, filed on Sep. 3, 2008.

(51) Int. Cl.
*A61B 18/02* (2006.01)
*F25D 3/00* (2006.01)
*F25D 19/00* (2006.01)

(52) U.S. Cl.
CPC . *A61B 18/02* (2013.01); *F25D 3/00* (2013.01); *F25D 19/00* (2013.01); *A61B 2018/0212* (2013.01); *F25B 2400/01* (2013.01)

(58) Field of Classification Search
CPC ............. A61B 2018/0001; A61B 2018/00017; A61B 2018/00023; A61B 2018/00035; A61B 2018/00005
USPC ..................................................... 606/20–26
See application file for complete search history.

(56) References Cited

U.S. PATENT DOCUMENTS

| 3,794,039 | A |   | 2/1974 | Kollner et al. |
| 4,082,096 | A |   | 4/1978 | Benson |
| 4,377,168 | A |   | 3/1983 | Rzasa et al. |
| 4,829,785 | A |   | 5/1989 | Hersey |
| 5,147,355 | A | * | 9/1992 | Friedman et al. ............... 606/23 |
| 5,237,824 | A |   | 8/1993 | Pawliszyn |
| 5,334,181 | A | * | 8/1994 | Rubinsky et al. ............... 606/22 |

(Continued)

FOREIGN PATENT DOCUMENTS

WO 2010028409 3/2010

OTHER PUBLICATIONS

Bartlett, Dean A. "The Fundamentals of Heat Exchangers." Industrial Physicist. (1996): 18-21. Print.*

(Continued)

*Primary Examiner* — Jaymi Della
(74) *Attorney, Agent, or Firm* — Pepper Hamilton, LLP (57) ABSTRACT

A cryogenic medical device for delivery of subcooled liquid cryogen to various configurations of cryoprobes is designed for the treatment of damaged, diseased, cancerous or other unwanted tissues. The device is a closed or semi-closed system in which the liquid cryogen is contained in both the supply and return stages. The device is capable of generating cryogen to a supercritical state and may be utilized in any rapid cooling systems. As designed, the device comprises a number of parts including a vacuum insulated outer dewar, submersible cryogen pump, baffled linear heat exchanger, multiple pressurization cartridges, a return chamber, and a series of valves to control the flow of the liquid cryogen. The cryogenic medical device promotes the subcooling to any external cryogenic instrument.

20 Claims, 5 Drawing Sheets

(56) References Cited

U.S. PATENT DOCUMENTS

| | | | |
|---|---|---|---|
| 5,423,807 A | 6/1995 | Milder | |
| 5,452,582 A | 9/1995 | Longsworth | |
| 5,674,218 A | 10/1997 | Rubinsky et al. | |
| 5,733,280 A | 3/1998 | Avitall | |
| 5,746,736 A * | 5/1998 | Tankovich | 606/9 |
| 5,758,505 A | 6/1998 | Dobak et al. | |
| 5,916,212 A | 6/1999 | Baust et al. | |
| 5,951,546 A | 9/1999 | Lorentzen | |
| 6,096,032 A | 8/2000 | Rowland | |
| 6,161,543 A | 12/2000 | Cox et al. | |
| 6,171,301 B1 | 1/2001 | Nelson et al. | |
| 6,306,129 B1 | 10/2001 | Little et al. | |
| 6,468,268 B1 | 10/2002 | Abboud et al. | |
| 6,468,269 B1 | 10/2002 | Korpan et al. | |
| 6,887,234 B2 | 5/2005 | Abboud et al. | |
| 7,160,291 B2 | 1/2007 | Damasco et al. | |
| 7,207,985 B2 | 4/2007 | Duong et al. | |
| 7,303,554 B2 | 12/2007 | Lalonde et al. | |
| 7,306,589 B2 | 12/2007 | Swanson | |
| 7,416,548 B2 | 8/2008 | Baust et al. | |
| 7,416,551 B2 | 8/2008 | Ad | |
| 2001/0021847 A1 * | 9/2001 | Abboud et al. | 606/21 |
| 2003/0055416 A1 | 3/2003 | Damasco et al. | |
| 2004/0215295 A1 * | 10/2004 | Littrup et al. | 607/96 |
| 2005/0090814 A1 | 4/2005 | Lalonde et al. | |
| 2005/0261671 A1 | 11/2005 | Baust et al. | |
| 2005/0261753 A1 * | 11/2005 | Littrup et al. | 607/96 |
| 2006/0079867 A1 | 4/2006 | Berzak et al. | |
| 2006/0129142 A1 | 6/2006 | Reynolds | |
| 2006/0235375 A1 | 10/2006 | Littrup et al. | |
| 2007/0021741 A1 | 1/2007 | Abboud et al. | |
| 2007/0233055 A1 | 10/2007 | Abboud et al. | |
| 2007/0244474 A1 | 10/2007 | DeLonzor et al. | |
| 2007/0277550 A1 | 12/2007 | Li et al. | |
| 2008/0009845 A1 | 1/2008 | Duong et al. | |
| 2008/0027422 A1 | 1/2008 | Vancelette et al. | |
| 2008/0147056 A1 | 6/2008 | van der Weide et al. | |
| 2008/0173028 A1 | 7/2008 | Littrup et al. | |
| 2008/0255551 A1 | 10/2008 | DeLonzor | |
| 2008/0300584 A1 | 12/2008 | Lentz et al. | |
| 2009/0012510 A1 | 1/2009 | Bertolero et al. | |
| 2009/0281533 A1 | 11/2009 | Ingle et al. | |
| 2009/0318913 A1 | 12/2009 | Li | |
| 2010/0057064 A1 | 3/2010 | Baust et al. | |
| 2010/0057067 A1 | 3/2010 | Baust et al. | |
| 2010/0241112 A1 | 9/2010 | Watson | |
| 2011/0152849 A1 | 6/2011 | Baust et al. | |

OTHER PUBLICATIONS

Fladerer at al. "Homogenous nucleation and droplet growth in supersaturated argon vapor: The cryogenic nucleation pulse chamber," Journal of Chemical Physics (2006), vol. 124. 2006 American Institute of Physics. USA.

* cited by examiner

MODULAR PULSED PRESSURE DEVICE FOR THE TRANSPORT OF LIQUID CRYOGEN TO A CRYOPROBE

RELATED APPLICATIONS

The present application claims priority to U.S. Provisional Patent Application Ser. No. 61/093,916 filed on Sep. 3, 2008 and titled Modular Pulsed Pressure Device for the Transport of Liquid Cryogen to a Cryoprobe, which is incorporated herein by reference in its entirety.

FIELD OF THE INVENTION

The present invention relates generally to the medical technology field and, in particular, to a medical device for use in a cryogenic system.

BACKGROUND OF THE INVENTION

Over a recent number of years, there has been a strong movement within the surgical community toward minimally invasive therapies. The main goals of the minimally invasive therapies include: 1) eradication of targeted tissue, 2) decreased hospitalization time, 3) limited postoperative morbidities, 4) shortened return interval to daily functions and work, and 5) reduced overall treatment cost. Cryotherapy is a minimally invasive method of treating a disease state through tissue freezing with thousands of patients now receiving the procedure annually. Currently, cryotherapy is used to treat numerous disease states including organ confined tumors such as prostate, kidney, liver, as well as cardiovascular disease, retinal detachment, pain management, and other illness/disease states.

Cryotherapy is an effective yet minimally invasive alternative to radical surgery and radiation therapy. The procedure is done under either general or epidural anesthesia. Since it is minimally invasive, it offers patients a quicker recovery and reduced severity of potential side effects. Without the expense associated with major surgery or an extended hospital stay, cryotherapy is a cost-effective treatment option.

The approaches utilized to date have focused on the delivery of liquid cryogen through the use of moderate to high pressure on the entire system or piston/bellows compression to drive fluid movement. At present, current systems utilizing liquid nitrogen operate at pressures between 14-480 psi; the systems in use cannot operate or withstand pressures greater that 500 psi. Further, the use of heat exchangers have been limited to coils placed into a bath of cryogen to allow for time consuming, inefficient passive subcooling of the cryogen in which activation of these devices circulate a cryogen (such as liquid nitrogen) to a probe to create a heat sink, thus resulting in tissue freezing.

There exists a need for improvements in cryotherapy, and medical devices or components associated with the treatment, to better circulate liquid cryogen to a cryoprobe, to provide for rapid delivery through small tubes, and to facilitate improved measures for treatment and cost. The medical device of the present invention will allow for the circulation (cooling, delivery, and return) of liquid cryogen to a cryoprobe for the freezing of targeted tissue. The invention will facilitate the eradication of tissue, decrease hospitalization time, limit postoperative morbidities, shorten return to daily functions and work, and further reduce the overall treatment cost. Desirably, these improvements to device design and application will also increase its utilization for the treatment of multiple disease states.

SUMMARY OF THE INVENTION

The following invention is a cryogenic medical device designed to deliver subcooled liquid cryogen to various configurations of cryoprobes for the treatment of damaged, diseased, cancerous or other unwanted tissues. The device is a closed or semi-closed system in which the liquid cryogen is contained in both the supply and return stages.

By converting liquid nitrogen to supercritical nitrogen (SCN) in a cylinder/cartridge cooled by atmospheric liquid nitrogen ($-196°$ C.), the SCN can be subcooled and tuned to the liquid phase, attaining an excess temperature. When the SCN is injected into one or more flexible cryoprobes, the SCN flows with minimal friction to the tip of the probe. In the tip, SCN pressure drops due to an increased volume and outflow restriction, heat is absorbed (nucleate boiling) along the inner surface of the tip, micro bubbles of nitrogen gas condense back into a liquid, and the warmed SCN reverts to pressurized liquid nitrogen as it exits the return tube and resupplies the dewar containing atmospheric liquid nitrogen. This flow dynamic occurs within a few seconds, typically in the order of 1 to 10 seconds depending on the probe or attachment configuration, and is regulated by a high pressure solenoid valve. Further, the cryosurgical procedure once instruments are in place can be performed with freeze times in ranges of about 15 seconds to 5 minutes (or ranges thereof), a drastic improvement over current known methods. (Therefore, consecutive freeze times over the course of the entire procedure significantly reduces time within the medical care setting, reducing overall health costs.) Upon emptying of the first cartridge subassembly, the process can be repeated with the second cartridge subassembly or any number of cartridges operated individually or in combination. Furthermore, embodiments of the present invention can be incorporated in any supercooling system or in delivering liquid cryogen to the desired instrument.

In one embodiment, the closed or semi-closed system has multiple pressurized cylinders filling and firing in sequence, and pressurized through a heating coil in one or more of the contained pressurized cylinders. The device is vented to the surrounding atmosphere through an adjustable pressure vent to prevent excess pressure buildup while in operation. The device comprises a number of parts including a vacuum insulated outer dewar, submersible cryogen pump, a series of self-pressurizing pulsatile delivery chambers, baffled linear heat exchanger, return chamber, and a series of valves to control the flow of the liquid cryogen. The outer dewar comprises a cryogenic apparatus having pressurizing pulsatile delivery chambers which drive liquid cryogen through the baffled linear heat exchanger. The linear heat exchanger comprises a tube-within-a-tube (i.e. chamber within a chamber configuration) whereby a vacuum is applied to the outer chamber to subcool an isolated reservoir of liquid cryogen. The inner chamber comprises a series of baffles and a central spiral to increase the flow path of the liquid cryogen while providing for increased contact-based surface area with the outer chamber to allow for more effective heat transfer and subcooling of the cryogen being delivered to the probe. Following circulation to the cryoprobe, cryogen (liquid and gas) is returned to the device into a return chamber which surrounds the supply chamber, thereby providing for a staged secondary subcooling chamber for the cryogen in the supply tube. The return chamber is open to the main dewar tank thereby allowing for exchange of liquid and gas between the supply and return chambers. Device operation is controlled and monitored by a series of pressure and vacuum valves designed to control the flow, cooling, and pressurization of the liquid cryogen. This control is achieved through various configurations of manual and computer controlled systems.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
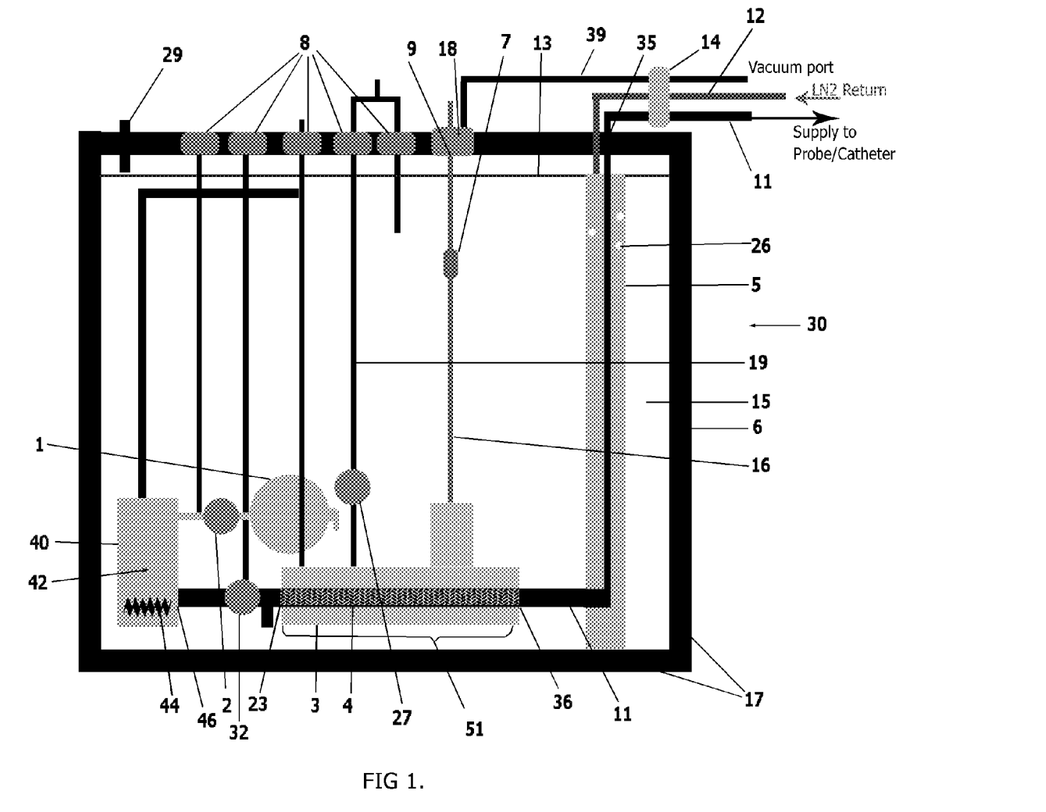
FIG. 1 is a side view of an illustrative embodiment of the device of the present invention.

An external view of a device and system in accordance with one embodiment of the present invention is shown in FIG. 1. The cryogenic system or device 30 has sidewalls 17 which form a container that encloses an internal cavity, or lumen 15. In an embodiment of FIG. 1, the container takes the form of a vacuum insulated dewar 6. The dewar 6 stores liquid cryogen and interconnects a supply line 11 and return line 12 to a probe or catheter (not shown) to form a closed system 30. The dewar 6 may be made of material such as stainless steel or any other material known for providing a vacuum insulated vessel. The dewar 6 is filled with liquid nitrogen or other liquefied gas (here, discussing as cryogen) to a maximum level 13. In one aspect, liquid nitrogen may be preferred. In another aspect, any fluidic cryogen may be utilized (e.g. argon, oxygen, helium, hydrogen).

Within the internal cavity 15 of the dewar 6 is a submersible pump 1 which delivers the liquid cryogen to a sealed pressurization apparatus 40. In one embodiment, a valve 2 controls the pressure fill into internal open chamber 42 of the pressurization apparatus 40. Once the cryogen enters the pressurization apparatus 40, an immersion heater 44 housed in the internal open chamber 42 heats the cryogen to create a desired pressure. The liquid nitrogen within the pressurized chamber starts at a temperature of about −196° C. When the heater is activated, it boils the nitrogen within the immediate area. Temperature within internal cavity 42 therefore stays within about −196° C. to −150° C., more typically in the range of about −196° C. to −160° C., or rather between about −170° C. to −160° C. Pressurized cryogen is then released through a valve 32 into the baffled linear heat exchanger. In one aspect, liquid nitrogen is converted to supercritical nitrogen (SCN) within the pressurization apparatus. The SCN is then directed to the heat exchanger for subcooling and tuned to the liquid phase to attain an excess temperature. Thereafter, the SCN can be injected into one or more flexible cryoprobes such that the SCN flows with minimal friction to the tip of the probe.

The baffled linear heat exchanger in one embodiment is surrounded by a subcooling chamber 3 which subcools the pressurized cryogen for delivery to external cryoprobes. The subcooling chamber 3 in connection with the heat exchanger 4 at an entrance 23 and an exit opening 36 form an integral unit 51 for supplying subcooled liquid cryogen. From the heat exchanger, the subcooled cryogen passes into a supply line 11 and continues out through an exit port 35 and through a control valve 14 where various configurations of cryoprobes are attached. The subcooling chamber may attach a vent line to any of the vents 8, to a supply connecting line 19 controlled through a valve 27, or to a vacuum line 16 through a control valve 7 which is connected to a vacuum pump 18.

The cryogen is returned (as demonstrated by the arrows in FIG. 1) from the cryoprobe via a return tube 12 into a return chamber/cylinder 5 of the dewar 6. The return tube 12 connects into the return cylinder 5 which also surrounds the supply tube 11 that exits the heat exchanger. One or more exit ports 35 may be included in a side wall 17 of the dewar 6 or may be a separate unit 14 to incorporate various control valves.

In operation, the device 30 is filled through a supply port 29 and then sealed to form a closed system, thereby allowing for the supply, return, collection, and reutilization of liquid cryogen during its utilization in the medical/surgical field. The entire system 30 may or may not be pressurized during operation. The system may also be vented to the surrounding environment to prevent excess pressure buildup during operation. In one aspect, the returning cryogen empties into the return cylinder or chamber 5. In another aspect, the returning cryogen may empty as bulk fluid into the internal lumen 15 within the dewar 6.

In one embodiment of the present invention, the linear heat exchanger subcools the liquid cryogen prior to delivery to tissue. In the embodiment of FIG. 1, the linear heat exchanger is an inner chamber 4 which passes through subcooling chamber 3 and is connected via the entrance 23 and exit opening 36. Liquid cryogen passing through the inner chamber 4 is reduced in temperature to a subcooling degree by the outer subcooling chamber 3. The chamber within a chamber configuration includes a subcooling vacuum chamber 3 filled with liquid cryogen upon which a vacuum 18 is drawn through valve-controlled port 9 to reduce the atmospheric pressure on the cryogen. The temperature of the cryogen within the subcooling chamber 3 can then be reduced even further. The subcooling chamber 3 also comprises valve controlled ports 8 external to the maximum liquid cryogen level for monitoring and electronically controlling temperatures, pressures, and flow rates of liquid cryogen passing through the subcooling unit. In one aspect, a vacuum 18 can be drawn on vacuum line 16 at a controlled internal valve 7 or external valve 9. In another aspect, valve controlled ports 8 may be accessible for delivery of liquid cryogen to the subcooling chamber 3 by way of a supply line 19 or as a vent 8 for any excessive gas coming from the subcooling chamber 3. As depicted in FIG. 1, the vacuum 18 also is attached to the cryoprobe(s) by way of vacuum line 39.

Figure 2A:
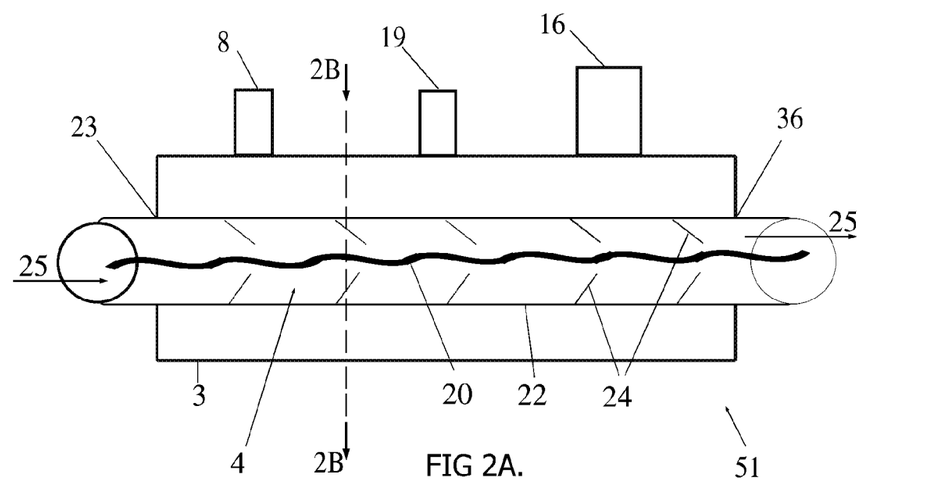
FIG. 2A is a side view of one embodiment of a heat exchanger of the present invention.
Figure 2B:
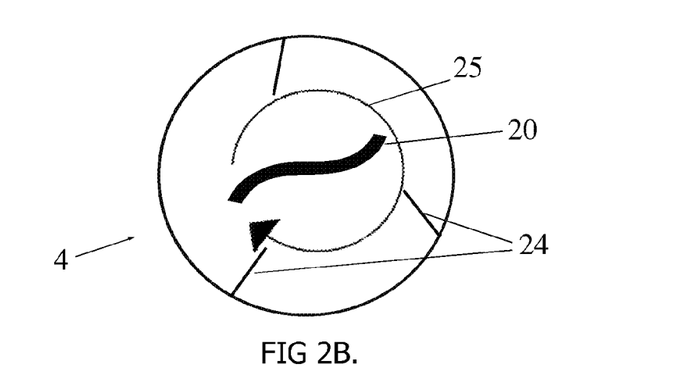
FIG. 2B is a cross-sectional view of FIG. 2A, a front view of one embodiment of a device of the present invention.
Figure 3A:
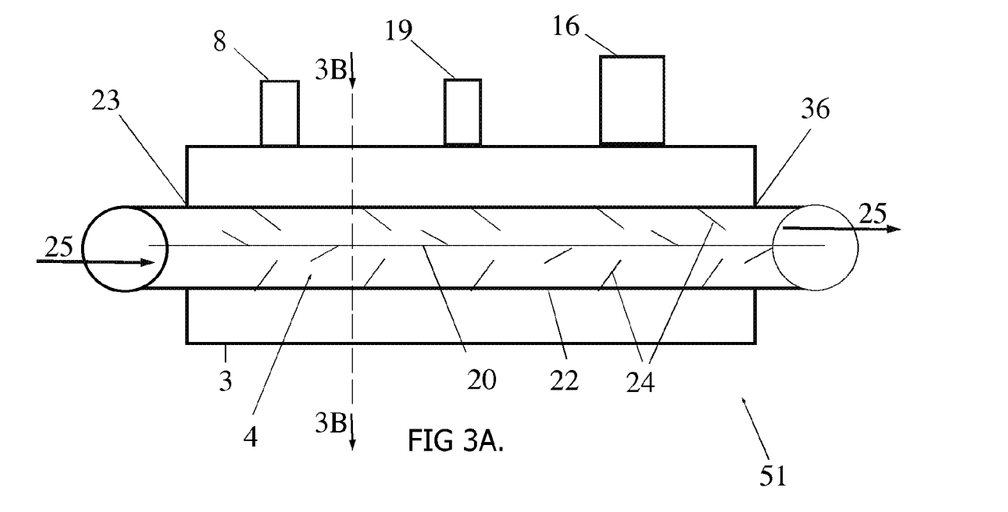
FIG. 3A illustrates a side view of one embodiment of a heat exchanger of the present invention.

Aspects of the linear heat exchanger are illustrated in FIGS. 2A, 2B and FIGS. 3A, 3B. FIG. 2A and FIG. 3A illustrate side views of different aspects of a linear baffled heat exchanger and subcooling unit 3 as an integral unit 51.

FIG. 2B depicts a cross-section of FIG. 2A; FIG. 2B is a front view of the linear baffled heat exchanger when looking into the inner chamber 4. An interior central component or spiral 20 within the interior lumen of the chamber 4 operates like a corkscrew to increase the flow path 25 of the liquid cryogen. An outer wall 22 of the inner chamber 4 also comprises baffles 24 which increase the surface area in the heat exchanger for quicker and reduced cooling of the liquid cryogen. As illustrated, a series of baffles 24 emanate into the flow path 25 (as illustrated by arrows) of the cryogen in the inner lumen, thereby increasing the surface area in the heat exchanger. The spiral component, however, may be any size and shape as to efficiently increase the flow of liquid cryogen. Planar structures, as described below, or any additional features included to increase surface area may be incorporated or substituted.

Figure 3B:
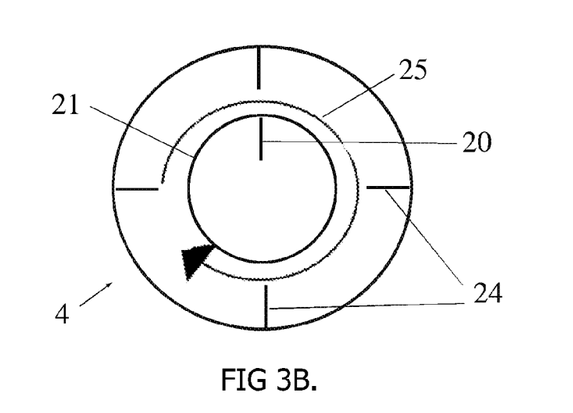
FIG. 3B is a cross-sectional view of FIG. 3A, one aspect of fluid flow through one embodiment of a heat exchanger of the device.

FIG. 3A illustrates another embodiment of a linear heat exchanger such that the internal structure 20 has a planar configuration and also operates in a circular motion to increase the flow 25 of the liquid cryogen. FIG. 3B depicts a cross-section of FIG. 3A such that the inner tubular unit 21 assists the internal structure 20 in circulating the flow of liquid cryogen through the interior lumen of the chamber 4.

One embodiment of the medical device comprises a return chamber 5 which is illustrated as a return cylinder 5 in FIG. 1 such that the return chamber 5 surrounds the supply line 11 coming from the heat exchanger. The return chamber 5 and the surrounded supply line may then provide a secondary heat exchanger for the system/medical device 30. Cryogen return is vented into the return chamber 5. In one aspect, the return chamber 5 comprises a series of vent holes 26 near the top of the return chamber 5 to allow for the venting of gas and/or liquid overflow into the main dewar 6. Vent holes 26 allow for the reutilization of cryogen and thus extend the operation time for the medical device 30.

In another aspect, the return tube 12 is vented into the main dewar 6 either directly or by first passing through a linear heat exchanger (similar to the combination of heat exchanger and subcooling chamber 3) to subcool the return cryogen prior to venting into the main dewar 6. Return of the cryogen to the main dewar 6 allows the cryogen to return through a heat exchanger such that the cryogen is reutilized and extends the operation time even longer.

In another embodiment, the medical device 30 may provide a system which is controlled through a series of computer controlled valves including any heaters, sensors, motors, or gauges. The sensors control and monitor pressure, temperature, and fluid level in the dewar, and can measure any metric as may be desired. In one aspect, the sensors monitor pressure levels within defined safety ranges. In another aspect, the sensors may control the pressurization of one or more components internal to the dewar. Any of the valves 2, 7, 8, 9, 27 or 32 including exit portal valve 14, may be automated to enable a controlled and consistent operation of the cryogenic system (e.g. computer controlled operation through the electronically controlled valves).

Figure 4:
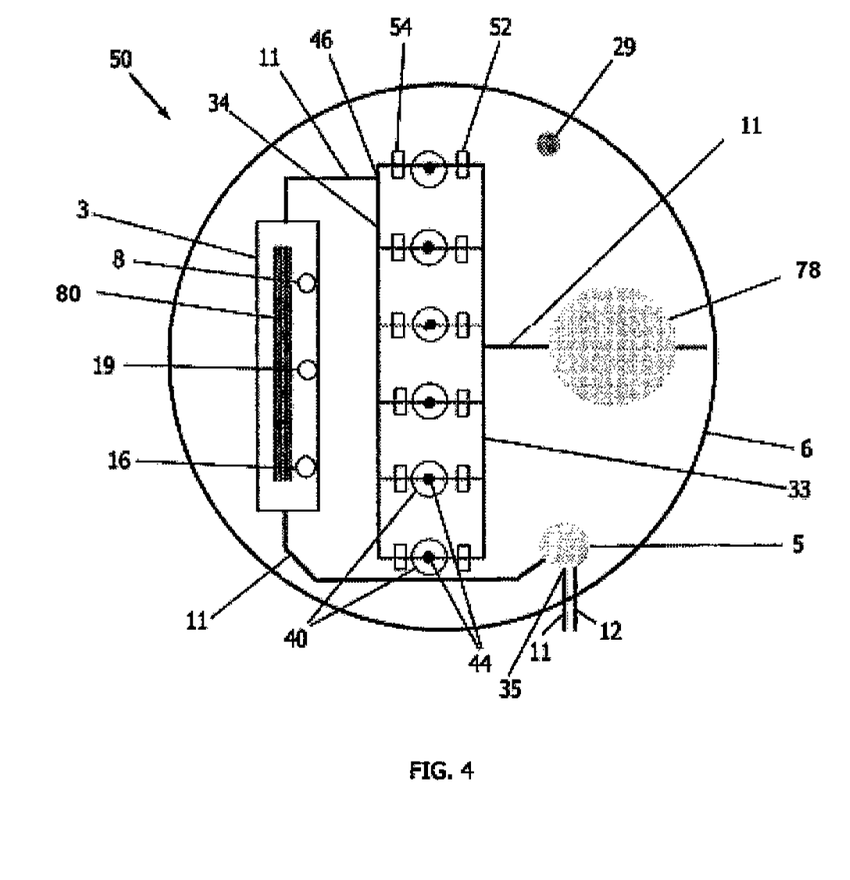
FIG. 4 is a top view of one embodiment of a device of the invention.

An embodiment of a system 50 is shown in FIG. 4. As illustrated in a top view of the system 50, a series of six pulsatile pressurization chambers 40 are sealed chambers/cylinders 40 within dewar 6 of the closed system 50. From the pump, liquid cryogen in pumped to the pulsatile pressurization chambers 40 which then delivers liquid cryogen in a continuous series of bursts to the heat exchanger 80. The baffled linear heat exchanger 80 provides an enhanced subcooling of the pressurized liquid cryogen while also incorporating an integral subcooling unit 3. The chambers 40, each comprising an individual immersion heater 44, can then sequentially deliver liquid cryogen at consistent rates, or as specifically determined rates, to the heat exchanger 80.

From the heat exchanger, the subcooled cryogen passes into a supply line 11 and continues out through an exit port 35 where a control valve 14 is positioned and various configurations of cryoprobes are attached. The cryogen is returned (as demonstrated by the arrows in FIG. 4) via a return tube 12 from the cryoprobe to the dewar 6 into a return cylinder 5. The return tube 12 connects into the return cylinder which surrounds the supply tube 11 that exits the heat exchanger 80. The entire system 50 may or may not be pressurized during operation. The device is also vented through vent ports 8 to the surrounding environment to prevent excess pressure buildup during operation.

During the operation of the system 50, as illustrated in the embodiment of FIG. 4, a cryogenic system 50 has been filled and detached from its cryogenic fill tank. In one embodiment, the system 50 is a separate mobile unit protected and contained entirely within an enclosed console for easy access and mobility. Once the system has been sealed, the cryogenic supply can be maintained for several procedures. The reutilization of the liquid cryogen provides a time savings and cost-efficient model for cryotherapeutic and cryosurgical procedures. The system 50 can be further utilized for any process requiring rapid cooling.

As depicted, the system 50 comprises a submersible liquid nitrogen pump 78 connected to a supply line 11 which directs the liquid nitrogen into a supply manifold 33. The supply manifold 33 routes the liquid nitrogen into at least one pulsatile pressurization chamber 40 where the liquid cryogen is heated. The pressurized liquid cryogen, here, liquid nitrogen, then starts filling the next pressurization cylinder/chamber 40 in the series such that when one chamber 40 is filling, another can be simultaneously pressurized and prepared for use. This permits a wave of activity through the cylinders so that it can cycle through each step of system operation. As the pressurized cryogen is delivered to the heat exchanger 80, and passes the subcooled pressurized cryogen out through the supply line 11 through the exit port 35 and into the attached cryoprobes, another pressurization chamber is filled and pressurized. The simultaneous use and pressurization of the liquid cryogen provides for the sequential delivery of liquid cryogen in a continuous series of pulsations to a cryogenic instrument or probe.

In one embodiment, liquid nitrogen is used; however, any cryogenic fluid may be utilized, including nitrogen, argon, helium, hydrogen, and other such desired fluids. Each pressurization apparatus 40 comprises a pressure valve controlled inlet 52, valve controlled outlet 54, and vent ports as may be desired, as well as an immersion heater 44. In one aspect, the filling of the pressurization apparati 40 is controlled through a series of pressure valves 52 on the supply manifold 33. Liquid cryogen is heated within each pressurized apparatus. Pressurized liquid cryogen is then released through the control valve 54 to an outlet port/opening 46 of an outlet manifold 34 to the supply line 11, and delivered to a baffled linear heat exchanger 80. In the illustrated embodiment, a subcooling unit 3 surrounds the heat exchanger 80 for more rapid cooling.

In one embodiment, the cryogenic device 50 comprises six pressurized apparati 40 linked together. Other embodiments, however, may comprise any number of pressurized apparati 40 individually or linked together in combination. The apparati can then be controlled individually or in sequence to deliver pressurized liquid cryogen to the heat exchanger 80. In another aspect, one or more pressurization apparati 40 may be arranged to supply one or more cryoprobes. Further, the series of pressurized apparati 40 may be interconnected with another series of apparati 40.

In one embodiment of FIG. 4, six pulsatile pressurization chambers 40 are housed within a support network of a console. In one example, three of the cylinders within one-half of the dewar simultaneously fill while three cylinders within the other half of the dewar deliver cryogen out through the outlet manifold. (Any number of cylinders, however, may be operated individually or in desirable combinations.) Liquid cryogen is heated in the sealed pressurization chambers 40. Pressure is increased to a specified level in the sealed pressurization chambers 40, and then the pressurized cryogen is controllably released into a heat exchanger 80 to subcool the cryogen. In one aspect, a subcooling vacuum chamber 3 surrounds the heat exchanger 80, facilitating the delivery of subcooled cryogen to an attached cryoprobe (also referred to as probe or catheter). As the pressurized cryogen is utilized, a sensor within the heat exchanger monitors the temperature and pressure of the subcooled cryogen passing into supply line 11 as it continues out through an exit port 35 where various configurations of cryoprobes are attached.

Although the system may fill or discharge each cylinder 40 individually, any simultaneous fill or discharge, or rate of fill or discharge, may be incorporated into the system. The closed system keeps a constant supply of liquid nitrogen available for delivery to the cryoprobe and provides a more immediate and rapid rate of cooling for cryotherapeutic procedures. It is therefore possible to close the supply port 29 where supply tanks fill the dewar (See FIG. 1 and FIG. 4) and move the system to any locale or setting. Furthermore, as depicted in FIG. 1, the supply valve 2 may be closed and the release valve 14 opened to create a flow of liquid cryogen to the cryoprobe. Various arrangements of valves and sensors may therefore provide for similar flow.

In one embodiment, the pressurized chambers 40 are filled and the dewar sealed. A single drive pump perpetuates directional flow of the cryogen into the pressurization chambers. In one embodiment, all chambers can be filled through various configurations of single direction pumping. In another embodiment, a reversible pump and fill method allows one pressurized chamber 40 to fill and then the pump flips or reverses functionality to fill another pressurized chamber. This process can be repeated to fill any number of chambers.

In one embodiment, pressurized chambers 40 are enclosed completely within the dewar 6. However, any arrangement of the pressurized cylinders is possible so long as the closed system provides for the pulsatile delivery of cryogen to the cryoprobe. As such, any single or multiple configurations of cryoprobes or catheters may be used. Such instruments may also include cryoguns or cryodevices for rapid cryo-delivery processes or cryotherapies.

Figure 5:
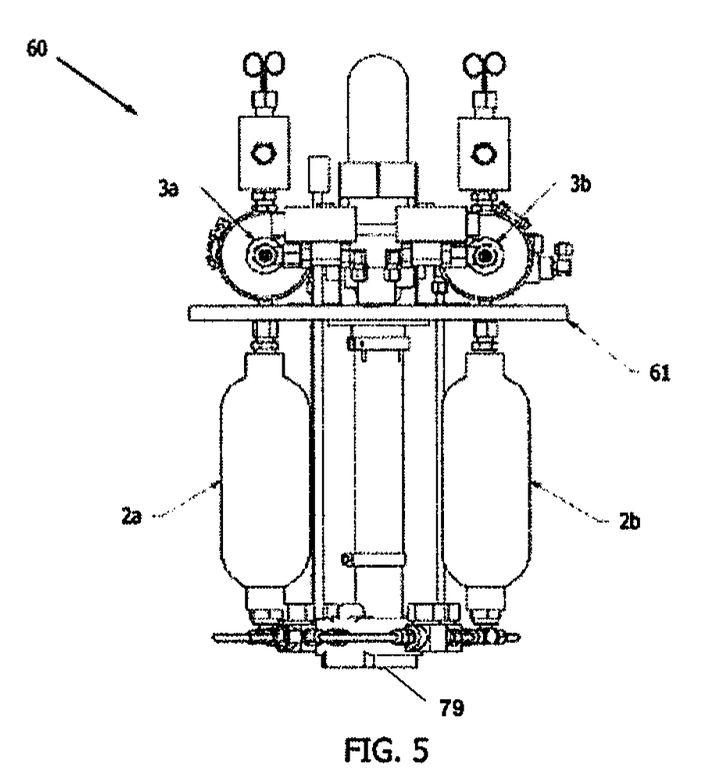
FIG. 5 is a depiction of a front view of the system.

As illustrated in FIG. 5, a cryogenic system 60 (also known as cryoengine 60) has a two cylinder configuration, the system of which is divided into two subassemblies: (I) those components above the cover 61 and (II) those components below the cover. All of the components below the cover are contained in a liquid nitrogen dewar and immersed in liquid nitrogen at atmospheric pressure (BP=−196° C.) during operation. To understand the operational features of the cryoengine and method of production and transport of supercritical nitrogen (SCN), a brief description of cryogen flow follows.

Upon filling the dewar (not pictured) with liquid nitrogen from an external source, an immersible liquid cryogen pump 79 is activated to fill each cryogen supply cylinder 2a & 2b, or cartridge, sequentially. Initially, one cartridge 2a is filled along with its linked cryogen pressurization cartridge 3a. Cryogenic solenoid valves provide venting of the gas within the cartridge assembly to support filling. Upon completion of the filling process, the cryogen pressurization cartridge 3a is heated to generate a pressure of about 1000 psi (68 bars). Liquid nitrogen becomes critical at about 493 psi (34 bar) (BP=−147° C.). Pressurization beyond the critical point results in the formation of SCN, a dense fluid without surface tension and capable of frictionless flow, and has properties that may be tuned to either a gas or liquid.

By converting liquid nitrogen to SCN in a cartridge cooled by atmospheric liquid nitrogen (−196° C.), the SCN is subcooled and tuned to the liquid phase, attaining an excess temperature (i.e. the ability to absorb heat without boiling) of approximately 50° C. When the SCN is injected into the flexible cryoprobe, the SCN flows with minimal friction to the tip of the probe (boiling chamber). In the tip, SCN pressure drops due to an increased volume and outflow restriction, heat is absorbed (nucleate boiling) along the inner surface of the TIP, micro bubbles of nitrogen gas condense back into a liquid, and the warmed SCN reverts to pressurized liquid nitrogen as it exits the return tube and resupplies the dewar containing atmospheric liquid nitrogen. This flow dynamic occurs within a few seconds and is regulated by a high pressure solenoid valve. Upon emptying of the first cartridge subassembly (2a & 3a), the process is repeated with the second cartridge subassembly (2b & 3b).

As demonstrated by FIG. 5, the limitations of liquid nitrogen have been overcome by developing a novel device to convert atmospheric liquid nitrogen to supercritical nitrogen. Where liquid nitrogen was previously delivered through large tubes and did not provide for rapid delivery, the current system herein described allows for rapid delivery of liquid cryogens through very small tubing. The SCN can be injected or drawn through two plus meters of hypodermic tubing without boiling, thereby resulting in near instantaneous ice formation at the tip to target site specific ablation of tissue as well as the creation of transmural lesions without the formation of a thrombus or aneurysm. Supercritical nitrogen is a dense fluid with properties of both gas and liquid that can be tuned toward one phase or the other. In the liquid phase, SCN lacks surface tension and transports without friction. The above-described technology generates SCN in a pressurized cartridge immersed in atmospheric liquid nitrogen. This cryoengine, which operates as a cryogen generator, produces SCN in the liquid phase with a boiling point of about −149° C. which is subcooled by the surrounding atmospheric liquid nitrogen to about −196° C. When the SCN is expelled from the device to the probe tip, the SCN passes instantly through the system without the phase transition to a gas due to both the frictionless flow and the subcooling which compensates for parasitic heat gain along the path. As such, the embodiment of FIG. 5 may be utilized in any supercooling system or in directing flow of liquid cryogen through to a cryo-instrument. The supercritical point will be determined by the chemistry of the specified liquid or gas used. Therefore, the system can be adjusted to accommodate for differences in chemistry.

In utilizing the medical device of the present invention, various methods in the industry may be employed in accordance with accepted cryogenic applications. As discussed, the embodiments of the present invention are for exemplary purposes only and not limitation. Advantageously, this device represents an important step in targeted thermal therapies. Various cryosurgical devices and procedures to apply freezing temperatures to a target tissue may be employed for use with the medical device of the present invention. The medical device of the present invention has been developed to enable and improve some of the approaches used to target or ablate tissue. Furthermore, the medical device can couple controlled pumping of a liquid cryogen through a baffled linear heat exchanger to decrease the overall temperature of the cryogen providing a greater heat capacity of the fluid and thereby resulting in an increased cooling potential in a cryoprobe.

Thus, the invention facilitates other improvements in cryotherapy, and medical devices or components associated with the treatment. The medical device of the invention allows for the circulation (cooling, delivery, and return) of liquid cryogen to a cryoprobe for the freezing of targeted tissue. The invention facilitates the eradication of tissue and can thereby decrease hospitalization time; and further limit postoperative morbidities, shorten return to daily functions and work, and further reduce the overall treatment cost. These improvements to device design and application can also increase utilization of the device for the treatment of multiple disease states.

The current device represents an improved development of cryosurgical devices by allowing for controlled linear flow of a cryogen without the need for high pressure or compression based bellows or piston systems. Further, the device contains a novel baffled linear heat exchanger designed for cryogen flow through a specialized subcooling chamber.

The embodiments of the present invention may be modified to take the shape of any device, container, apparatus, or vessel currently used in industry. Specifically, cylindrical or alternative vessels may provide containers for the cryogenic system for improved cryogenic supply and delivery. Further, any compartmental arrangement in combination with the components of the above system may take many forms and be of any size, shape, or passageway. Any number of vents may also be utilized to facilitate operation of the system. The system may also be a partially closed or completely closed system.

In one embodiment of the system, the device is contained within a console, a shell or enclosure that allows the system to be easily transported. The enclosure may then include any mobile feature such as wheels, handles, and fixtures (or allow placement onto a cart having these features) so that the system can be transported to and from the location of treatment. Such mobility allows the system to be easily moved to and from an operating room or site of therapeutic treatment. It is also noted that the system is readily separable from the cryogen fill tanks and fill lines that initially supply the system with the liquid nitrogen or other such cryogenic fluid at the supply port 29 (As shown in FIG. 1). This improved feature eliminates the bulkiness of standard cryogenic medical devices.

As presented, the multiple embodiments of the present invention offer several improvements over standard medical devices currently used in cryogenic industry. The improved cryogenic medical devices remarkably enhance its utilization for the cooling, delivery and return of a liquid cryogen to a cryoprobe for the freezing of targeted tissue. The present invention provides cost savings and significantly reduced treatment times which further reduce expenditures in the healthcare setting. The previously unforeseen benefits have been realized and conveniently offer advantages for the treatment of multiple disease states. In addition, the improvements enable construction of the device as designed to enable easy handling, storage, and accessibility. Further uses of the system outside of the healthcare setting are foreseeable. Potential uses in the space industry, defense systems or any industry requiring rapid cooling may incorporate the cryogenic system as thus described.

As exemplified, the device may include any unitary structure, vessel, device or flask with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A cryogenic system comprising:
   a) a container capable of holding cryogen within said container;
   b) one or more cryoprobes outside said container for use in cryotherapeutic procedures;
   c) a pressurization apparatus disposed within said container and having
      i) an internal chamber capable of containing the cryogen,
      ii) exterior surfaces configured to come into contact with the cryogen held within said container to provide thermal communication between the cryogen contained in the internal chamber and the cryogen held within said container,
      iii) an inlet port for filling the internal chamber of said pressurization apparatus with the cryogen,
      iv) one or more heaters arranged inside the internal chamber of said pressurization apparatus, wherein said one or more heaters being capable of pressurizing the cryogen in the internal chamber to form pressurized cryogen when the internal chamber contains the cryogen and said one or more heaters is activated, said internal chamber being capable of containing said pressurized cryogen formed by pressurizing the cryogen in the internal chamber, and
      v) an outlet port for releasing the pressurized cryogen from said pressurization apparatus;
   d) a first valve, wherein said first valve is connected to the inlet port of the pressurization apparatus;
   e) a second valve, wherein said second valve is connected to the outlet port of the pressurization apparatus;
   f) a heat exchanger included in said container for submersion in the cryogen and being connected to the second valve;
   g) a pump included in said container for complete submersion in the cryogen in the container, wherein:
      i) the pump is connected to the first valve and is configured to deliver the cryogen from within said container when said container is holding the cryogen through the first valve into the internal chamber of the pressurization apparatus; and
      ii) the pressurization apparatus connects to said heat exchanger through the second valve; and
   h) at least one supply line connected to said heat exchanger and capable of directing and transporting to said one or more cryoprobes, the pressurized cryogen from the heat exchanger,
   wherein said cryogenic system is housed within a transportable console and separate from one or more cryogenic fill tanks.

2. The cryogenic system of claim 1, further comprising at least one return line i) connecting said one or more cryoprobes to said container, and ii) being configured to return the pressurized cryogen from said one or more cryoprobes to said container.

3. The cryogenic system of claim 2, further comprising the cryogen in said container, said exterior surfaces of the pressurization apparatus are in contact with the cryogen within said container, said internal chamber contains the pressurized cryogen generated from the cryogen in the internal chamber by activation of said one or more heaters, said heat exchanger is submersed in the cryogen in said container, said pump is submersed in the cryogen in said container, said at least one supply line contains the pressurized cryogen from the heat exchanger, and said at least one return line contains a return cryogen formed from said pressurized cryogen from said one or more cryoprobes, said return cryogen in said at least one return line being at a lower pressure than said pressurized cryogen in said at least one supply line.

4. The cryogenic system of claim 3, wherein said return cryogen is liquid nitrogen.

5. The cryogenic system of claim 3, wherein said pressurized cryogen in said pressurization apparatus is the supercritical cryogen.

6. The cryogenic system of claim 5, wherein said supercritical cryogen is supercritical nitrogen.

7. The cryogenic system of claim 6, wherein said pressurization apparatus is configured to be filled with the supercritical nitrogen pressurized to about 1000 psi.

8. The cryogenic system of claim 1, wherein said heat exchanger is a baffled linear heat exchanger.

9. The cryogenic system of claim 1, further comprising said cryogen in said container, wherein:

said exterior surfaces of the pressurization apparatus are in contact with the cryogen within said container, said internal chamber contains the pressurized cryogen generated from the cryogen in the internal chamber by activation of said one or more heaters, said heat exchanger is submersed in the cryogen in said container, said pump is submersed in the cryogen in said container, and said at least one supply line contains the pressurized cryogen from the heat exchanger.

10. The cryogenic system of claim 9, wherein said cryogen within said container is liquid nitrogen.

11. The cryogenic system of claim 9, wherein said pressurized cryogen in said pressurization apparatus is supercritical cryogen.

12. The cryogenic system of claim 11, wherein said supercritical cryogen is supercritical nitrogen.

13. The cryogenic system of claim 12, wherein said pressurization apparatus is configured to be filled with the supercritical nitrogen pressurized to about 1000 psi.

14. The cryogenic system of claim 1, wherein said heat exchanger is surrounded by a subcooling chamber.

15. A cryogenic system for generating supercritical nitrogen, said cryogenic system comprising:
a) a dewar capable of holding liquid nitrogen within said dewar;
b) a cryogen supply cylinder linked to a pressurization cartridge, said cryogen supply cylinder positioned in said dewar and positioned to come into contact with said liquid nitrogen in said dewar when said dewar is holding said liquid nitrogen to provide thermal communication between an interior of said cryogen supply cylinder and said liquid nitrogen in said dewar when said dewar is holding said liquid nitrogen, and said pressurization cartridge positioned to be out of contact with said liquid nitrogen in said dewar, said cryogen supply cylinder linked to said pressurization cartridge configured to be filled with said liquid nitrogen and being capable of containing said supercritical nitrogen generated by said cryogenic system and pressurized to about 1000 psi, and said cryogen supply cylinder that is in contact with said liquid nitrogen in said dewar is configured to subcool said supercritical nitrogen;
c) a submersible pump connected to said cryogen supply cylinder for pumping said liquid nitrogen from said dewar into said cryogen supply cylinder, said submersible pump being completely disposed in said dewar;
d) at least one immersion heater capable of generating said supercritical nitrogen from said liquid nitrogen in said cryogen supply cylinder linked to said pressurization cartridge by activation of said at least one immersion heater;
e) a cryoprobe;
f) tubing connecting said cryogen supply cylinder linked to said pressurization cartridge to said cryoprobe; and
g) a return tube connecting the cryoprobe to the dewar,
wherein said cryogenic system is housed within a transportable console and separate from one or more cryogenic fill tanks.

16. The cryogenic system of claim 15, further comprising said liquid nitrogen in said dewar, wherein:
said cryogen supply cylinder linked to said pressurization cartridge being filled with said liquid nitrogen and pressurized to about 1000 psi by activation of said at least one immersion heater to generate said supercritical nitrogen; and
said tubing containing said supercritical nitrogen from said cryogen supply cylinder linked to said pressurization cartridge.

17. A cryogenic system for generating supercritical nitrogen, said cryogenic system comprising:
a) a dewar comprising liquid nitrogen;
b) a cryogen supply cylinder linked to a pressurization cartridge, said cryogen supply cylinder positioned in said dewar positioned to come into contact with said liquid nitrogen in said dewar to provide thermal communication between an interior of said cryogen supply cylinder and said liquid nitrogen in said dewar, and said pressurization cartridge positioned to be out of contact with said liquid nitrogen in said dewar, said cryogen supply cylinder (i) linked to said pressurization cartridge, (ii) filled with said liquid nitrogen and (iii) comprising at least one immersion heater for pressurizing said cryogen supply cylinder to about 1000 psi upon activation of said at least one immersion heater, generating said supercritical nitrogen from said liquid nitrogen in said cryogen supply cylinder wherein said cryogen supply cylinder that is in contact with said liquid nitrogen in said dewar is configured to subcool said supercritical nitrogen;
c) a submersible pump connected to said cryogen supply cylinder for pumping said liquid nitrogen from said dewar into said cryogen supply cylinder, said submersible pump being completely disposed in said dewar;
d) a cryoprobe;
e) tubing connecting said cryogen supply cylinder linked to said pressurization cartridge to said cryoprobe, said tubing containing said supercritical nitrogen from said cryogen supply cylinder linked to said pressurization cartridge; and
f) a return tube connecting the cryoprobe to the dewar.

18. A method of delivering pressurized cryogen to one or more cryoprobes, said method comprising the steps of:
providing a cryogenic system comprising:

a) a container holding cryogen;
b) the one or more cryoprobes outside said container for use in cryotherapeutic procedures;
c) a pressurization apparatus disposed within said container and having
   i) an internal chamber capable of containing the cryogen,
   ii) exterior surfaces configured to come into contact with the cryogen held within said container to provide thermal communication between the cryogen contained in the internal chamber and the cryogen held within said container,
   iii) an inlet port for filling the internal chamber of said pressurization apparatus with the cryogen,
   iv) one or more heaters arranged inside the internal chamber of said pressurization apparatus, wherein said one or more heaters being capable of pressurizing the cryogen in the internal chamber to form the pressurized cryogen when the internal chamber contains the cryogen and said one or more heaters is activated, said internal chamber being capable of containing said pressurized cryogen formed by pressurizing the cryogen in the internal chamber, and
   v) an outlet port for releasing the pressurized cryogen from said pressurization apparatus;
d) a first valve, wherein said first valve is connected to the inlet port of the pressurization apparatus;
e) a second valve, wherein said second valve is connected to the outlet port of the pressurization apparatus;
f) a heat exchanger included in said container for submersion in the cryogen and being connected to the second valve;
g) a pump included in said container for complete submersion in the cryogen in the container, wherein:
   i) the pump is connected to the first valve and is configured to deliver the cryogen from within said container when said container is holding the cryogen through the first valve into the internal chamber of the pressurization apparatus; and
   ii) the pressurization apparatus connects to said heat exchanger through the second valve; and
h) at least one supply line connected to said heat exchanger and capable of directing and transporting to said one or more cryoprobes, the pressurized cryogen from the heat exchanger, wherein said cryogenic system is housed within a transportable console and separate from one or more cryogenic fill tanks;

pumping the cryogen from within said container through the first valve and the inlet port and into the internal chamber of the pressurization apparatus using the pump submersed in the cryogen in said container;

activating the one or more heaters arranged inside the internal chamber of said pressurization apparatus to increase pressure of the cryogen to generate the pressurized cryogen in the internal chamber;

delivering said pressurized cryogen from the internal chamber of said pressurization apparatus through the second valve and the outlet port and to the heat exchanger; and delivering said pressurized cryogen from the heat exchanger through said at least one supply line to the one or more cryoprobes.

19. The method of claim 18, wherein the pressurized cryogen in said pressurization apparatus is a supercritical cryogen.

20. The method of claim 19, wherein the supercritical cryogen is supercritical nitrogen.

\* \* \* \* \*